United States Patent
Palmer et al.

(10) Patent No.: US 9,121,824 B2
(45) Date of Patent: Sep. 1, 2015

(54) FLUIDIC AND ELECTRICAL INTERFACE FOR MICROFLUIDIC CHIPS

(71) Applicants: James T. Palmer, Loveland, CO (US); Philippe M. Dekleva, Fort Collins, CO (US)

(72) Inventors: James T. Palmer, Loveland, CO (US); Philippe M. Dekleva, Fort Collins, CO (US)

(73) Assignee: METTLER-TOLEDO THORNTON, INC., Bedford, MA (US)

( * ) Notice: Subject to any disclaimer, the term of this patent is extended or adjusted under 35 U.S.C. 154(b) by 127 days.

(21) Appl. No.: 13/677,036

(22) Filed: Nov. 14, 2012

(65) Prior Publication Data

US 2013/0313116 A1 Nov. 28, 2013

Related U.S. Application Data

(60) Provisional application No. 61/559,497, filed on Nov. 14, 2011.

(51) Int. Cl.
  *G01N 27/447* (2006.01)
  *B81B 1/00* (2006.01)
  (Continued)

(52) U.S. Cl.
  CPC ...... *G01N 27/44791* (2013.01); *B01L 3/50273* (2013.01); *B01L 3/502715* (2013.01); *B01L 9/527* (2013.01); *B81B 1/00* (2013.01);
  (Continued)

(58) Field of Classification Search
  CPC .................................. B01L 2/5027–2/502792
  USPC ......... 435/283.1, 288.4, 288.3; 422/502, 504, 422/503, 50, 501; 436/43; 204/601, 451, 204/453, 604; 137/833
  See application file for complete search history.

(56) References Cited

U.S. PATENT DOCUMENTS

2002/0155033 A1  10/2002  Strand et al.
2005/0145787 A1   7/2005  Prosser et al.
(Continued)

FOREIGN PATENT DOCUMENTS

WO  WO2005075081  8/2005

OTHER PUBLICATIONS

International Search Report, International Searching Authority, Feb. 20, 2013, pp. 1-8.
(Continued)

*Primary Examiner* — J. Christopher Ball
(74) *Attorney, Agent, or Firm* — Samuel M. Freund; Cochran Freund & Young LLC

(57) ABSTRACT

A microfluidic chip interface for providing fluid communication with external fluid sources and external fluid waste containers, and for providing electrical contact with voltage sources and voltage and current measuring devices, is described. The microchip is first placed into electrical communication with at least one electrical source and at least one electronic measurement device, and reversibly secured in place. Chosen fluids are provided into the microchip and directed through the chip using a fluid manifold having dispensing tubes and fluid aspiration tubes, which is brought into the vicinity of the secured microchip. The distance between the fluid manifold and the microchip is chosen such that the injection tubes are located within wells in the microchip connected to microfluidic channels, and the aspiration tubes are located near the surface of the microchip in the vicinity of the wells such that fluid spillage onto the surface of the microchip during fluid transfer is avoided. The fluid manifold is removed from fluid communication with the microchip during electrical measurements.

21 Claims, 10 Drawing Sheets

(51) Int. Cl.
  *B01L 3/00* (2006.01)
  *B01L 9/00* (2006.01)
  *G01N 35/00* (2006.01)

(52) U.S. Cl.
  CPC ... *G01N35/00069* (2013.01); *B01L 2300/0816* (2013.01); *B01L 2400/049* (2013.01); *B01L 2400/0421* (2013.01); *Y10T 29/49117* (2015.01)

(56) References Cited

U.S. PATENT DOCUMENTS

| | | |
|---|---|---|
| 2005/0191212 A1 | 9/2005 | Antocci et al. |
| 2005/0255001 A1 | 11/2005 | Padmanabhan et al. |
| 2005/0284213 A1 | 12/2005 | Karp et al. |
| 2006/0073484 A1 | 4/2006 | Mathies et al. |
| 2006/0257992 A1 | 11/2006 | McDevitt et al. |
| 2007/0025887 A1 | 2/2007 | Baeuerle et al. |
| 2007/0157973 A1 | 7/2007 | Chien et al. |
| 2009/0145485 A1 | 6/2009 | Smith et al. |
| 2009/0165876 A1 | 7/2009 | Atkin et al. |
| 2009/0253181 A1 | 10/2009 | Vangbo et al. |
| 2009/0283408 A1 | 11/2009 | Prak et al. |
| 2010/0165784 A1 | 7/2010 | Jovanovich et al. |
| 2010/0200402 A1 | 8/2010 | Li et al. |
| 2011/0229961 A1 | 9/2011 | Higashi et al. |

OTHER PUBLICATIONS

Mosadegh et al., "Next-generation integrated microfluidic circuits," Lab on a Chip Miniaturisation for chemistry, physics, biology and bioengineering, 2011, 11, 2813-2818.

Extended European Search Report, European Patent Office, U.S. Appl. No. 12849212.1, pp. 1-26, Apr. 22, 2015.

FLUIDIC AND ELECTRICAL INTERFACE FOR MICROFLUIDIC CHIPS

CROSS-REFERENCE TO RELATED APPLICATIONS

The present application claims the benefit of U.S. Provisional Patent Application No. 61/559,497 for "Fluidic And Electrical Interface For Microfluidic Chips" which was filed on Nov. 14, 2011, the entire contents of which is hereby specifically incorporated by reference herein for all that it discloses and teaches.

FIELD OF THE INVENTION

The present invention relates generally microfluidic chips suitable for capillary electrophoresis as an example and, more particularly, to a fluidic and electrical interface effective for transferring fluids from external fluid sources through a microfluidic chip to external waste containers, and for providing electrical contact to the microfluidic chip to enable measurements to be made on the fluids.

BACKGROUND OF THE INVENTION

Microfluidic chips find use in many areas such as fluid mixing for chemical reactions, cell sorting, and electrophoresis, as examples, and often have both electrical terminals and microfluidic channels in which electrokinetic phenomena, which include electro-osmotic flow and electrophoresis, are generated.

Microfluidic chips suitable for capillary electrophoresis typically provide a carrier channel in which substances within a sample are separated by electrophoresis and detected, and a sample channel in fluid communication with the carrier channel for introducing samples into the carrier channel. Generally, samples and carrier fluids are manually introduced into the microchip by dropper, syringe, and the like, and these fluids flow through a network of channels by capillary action, external pressure or electro-osmotic flow. Voltages between a few hundred volts and greater than one thousand volts may be applied to the channels using electrical probes, for inducing electrophoretic and/or electro-osmotic flow useful for introducing small amounts of the sample fluid into the carrier channel at an intersection of the two channels. As stated, charged substances in the sample will separate in the carrier channel as a consequence of differences in electrophoretic mobility. At chosen locations, the fluid in the carrier channel may be optically or electrically interrogated yielding component analysis information for the sample.

Although certain substances within a sample fluid may be efficiently separated for analysis using conventional microfluidic chips for capillary electrophoresis, the handling, timing and delivery of very small fluid volumes to flow paths in the chip, along with the manual transfer of fluids to corresponding reservoirs, renders automated capillary electrophoresis for sample analysis difficult.

SUMMARY OF THE INVENTION

Embodiments of the present invention overcome the disadvantages and limitations of the prior art by providing a microfluidic interface which cooperates with a microfluidic chip to provide fluid from one or more external fluid sources to flow paths within the chip without spilling or leaving fluid on the surface of the chip.

Another object of embodiments of the invention is to provide an interface between a voltage source, generally a high voltage source, and electrical measurement apparatus and a microfluidic chip.

Yet another object of embodiments of the invention is to provide an interface between a voltage source and a microfluidic chip effective for separating components in a sample by capillary electrophoresis.

Still another object of embodiments of the invention is to provide an interface between a current measuring device and a microfluidic chip for analysis of the separated components.

Another object of embodiments of the invention is to provide an interface for permitting a variety of sample handling and sample analyses within a microfluidic chip.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and, in accordance with the purposes of the present invention as embodied and broadly described herein, the apparatus for establishing a fluidic and electrical interface to a microfluidic chip having a top surface and at least two wells opening to the top surface, hereof, includes: a microchip tray for receiving and holding the microfluidic chip; an electrical bus adapted for electrical communication with at least one voltage source and at least one electronic measurement device; a microchip tray slide adapted for receiving the microchip tray and placing the microchip into electrical communication with the electrical bus and for reversibly securing the microchip tray and the microchip in electrical communication therewith; a fluid manifold assembly for providing chosen fluids to the microchip and for aspirating the chosen fluids from the wells of the microchip, the fluid manifold assembly including: an electrolyte pump; a sample pump; a vacuum pump; and a fluid manifold including: at least two liquid dispensing tubes for establishing fluid communication with either the electrolyte pump or the sample pump and the at least two wells, one of the dispensing tubes in fluid communication with one of the at least two wells; and at least two liquid aspiration tubes for establishing fluid communication with said vacuum pump, one of the aspiration tubes in fluid communication with one of the at least two wells; a fluid manifold mounting plate for holding the fluid manifold; a pushrod having a first end and a second end, the first end of said pushrod affixed to the fluid manifold mounting plate; a pivoted rocker arm for driving the pushrod toward or away from the microchip; a cam for causing the rocker arm to pivot; a motor for rotating the cam; and at least one spring for causing the pushrod to follow the rocker arm and the rocker arm to follow the cam; whereby the fluid manifold is disposed a chosen distance from the microchip for establishing fluid communication between the at least two liquid dispensing tubes and the at least two liquid aspiration tubes and the at least two wells, and at greater than the chosen distance for electrical measurements.

In another aspect of the invention and, in accordance with its objects and purposes, the apparatus for establishing a fluidic and electrical interface to a microfluidic chip having a top surface and at least two wells opening to the top surface, hereof, includes: a microchip tray for receiving and holding the microfluidic chip; an electrical bus adapted for electrical communication with at least one voltage source and at least one electronic measurement device; means for placing the microchip into electrical communication with the electrical bus and for reversibly securing the microchip tray and the microchip in electrical communication therewith; a fluid manifold assembly for providing chosen fluids to the microchip and for aspirating the chosen fluids from the wells of the microchip, said fluid manifold assembly including: an electrolyte pump; a sample pump; a vacuum pump; and a fluid manifold including: at least two liquid dispensing tubes for establishing fluid communication with either the electrolyte pump or the sample pump, and the at least two wells, one of the dispensing tubes in fluid communication with one of the at least two wells; and at least two liquid aspiration tubes for establishing fluid communication with the vacuum pump, one of the aspiration tubes in fluid communication with one of the at least two wells; means for moving the fluid manifold to a chosen distance from the microchip for establishing fluid communication between the at least two liquid dispensing tubes and the at least two liquid aspiration tubes and the at least two wells, and to a greater than the chosen distance for electrical measurements.

In yet another aspect of the invention and, in accordance with its objects and purposes, the method for providing a fluidic and an electrical interface for a microfluidic chip having a top surface at least two wells opening to the top surface, hereof includes: placing the microchip into electrical communication with an electrical bus capable of electrical communication with at least one voltage source and at least one electronic measurement device; reversibly securing the microchip in electrical contact with the bus; providing chosen fluids to the wells of the microchip using a fluid manifold having one injection tube and one aspiration tube for each well; moving the fluid manifold to a chosen distance from the secured microchip, whereby each injection tube is disposed in its corresponding well, and each aspiration tube is disposed near the surface of the microchip in the vicinity of a well, such that fluid does not spread over the top surface of the microchip during said step of providing chosen fluids to the wells, and to a greater than the chosen distance for electrical measurements.

Benefits and advantages of the present invention include, but are not limited to, providing a microfluidic chip interface for reliably and reproducibly flushing fluids from external sources through the wells of the microchip to external waste containers, in a manner that prevents fluid films from spreading across the top surface of the microchip that can divert the driving current from the capillary elements in the microchip. Another benefit is the establishment of electrical contact with the microfluidic chip for delivering chosen voltages and enabling current and voltage measurements to be made on the fluid components.

BRIEF DESCRIPTION OF THE DRAWINGS

The accompanying drawings, which are incorporated in and form a part of the specification, illustrate embodiments of the present invention which, together with the description, serve to explain the principles of the invention. In the drawings:

FIG. 1A is a schematic representation of an embodiment of the manifold assembly of the present invention effective for filling and flushing (dispensing) various fluid wells of a microchip with sample solutions and/or standard solutions, or with background electrolyte, and for aspirating these wells, while

FIG. 6A is a schematic representation of a front perspective view of the fluid manifold assembly illustrated in FIG. 2 hereof, showing the mounting block for the spring-loaded, rocker arm, the pushrod-actuated manifold mounting plate and the guide rods therefor, while

FIG. 7A is a schematic representation of a front perspective view of the fluid manifold mounting plate, with the manifold disposed slightly above a microchip, illustrating the injection and aspirate tubes in proximity to their insertion locations in wells in the microchip, while

DETAILED DESCRIPTION OF THE INVENTION

Briefly, embodiments of the present invention include a fluidic and electrical interface effective for transferring fluids from external fluid sources through microfluidic channels in a microfluidic chip to external waste containers, and for providing electrical contact to the chip for enabling measurements to be made on the fluid components. As used herein, the terms chip and microchip are intended to mean a microfluidic chip.

Figure 1A:
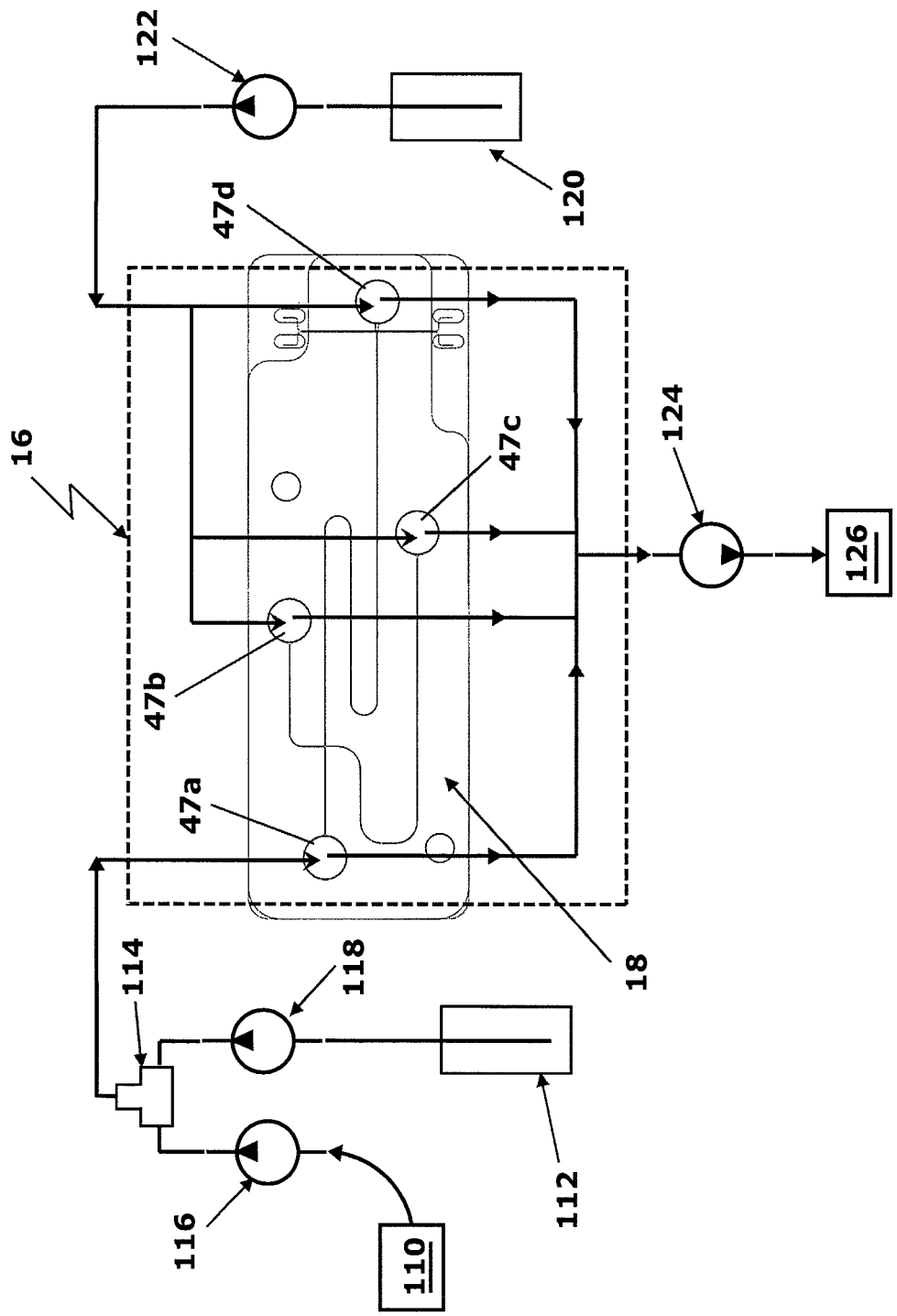
Figure 1B:
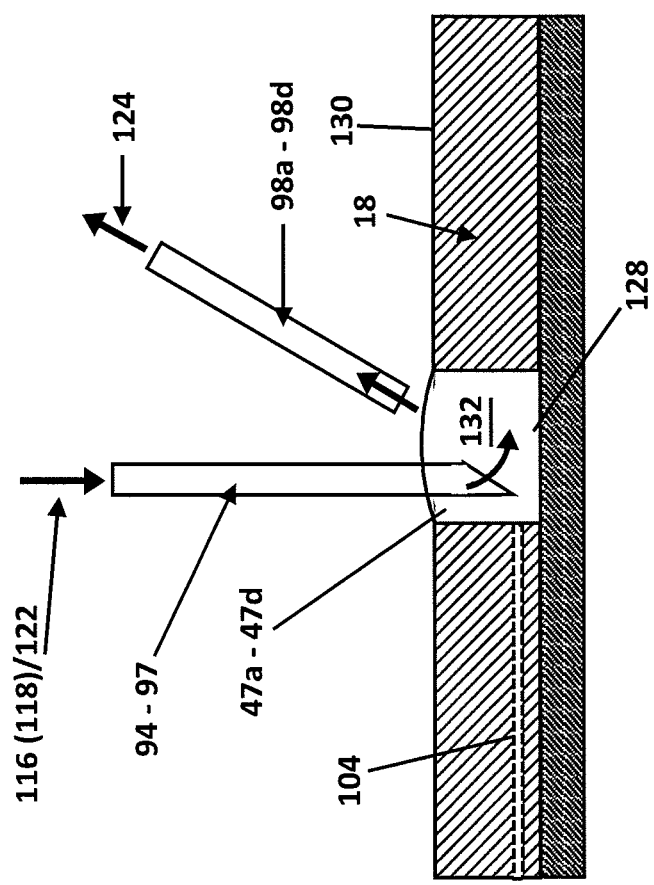
FIG. 1B is a schematic representation of the disposition of a dispensing tube and an aspiration tube in a fluid well of the microchip shown in FIG. 1A hereof.

Reference will now be made in detail to the present embodiments of the invention, examples of which are illustrated in the accompanying drawings. In what follows, similar or identical structure will be identified using identical reference characters. Turning now to FIG. 1A, a schematic representation of an embodiment of a fluid manifold assembly including fluid manifold, 16, of the present invention effective for filling and flushing (dispensing fluid to) fluid well, 47a, of microchip, 18, with sample solution from source, 110, and with an internal standard solution from source, 112, if desired, through mixer, 114, using pumps, 116, and, 118, respectively, for filling and flushing fluid wells, 47b-47d, with background electrolyte from source, 120, using pump, 122, and for aspirating the wells 47a-47d using aspiration pump, 124, which pumps fluid to waste receptacle 126. FIG. 1B is a schematic representation of narrow-bore (0.5 mm) dispensing tubes, 94-97 (FIG. 6B), and narrow-bore (0.5 mm) aspiration tubes, 98a-98d (FIG. 6B), which may be cut at an angle, in relationship to fluid well 47a-47d of microchip 18 shown in FIG. 1A hereof. Shown also in FIG. 1B is microfluidic channel, 104 (FIG. 7B).

As will be described in more detail hereinbelow, manifold 16 including dispensing and aspiration tubes is raised and lowered relative to chip 18. As seen in FIGS. 1A and 1B, narrow-bore tubes 94-97 extend from the bottom of manifold 16 and enter wells 47a-47d of microchip 18 to a position near the bottom, 128, thereof. Typical distances from the bottom of the wells may be from about 0 mm to about 3 mm, shorter distances generating beneficial fluid mixing in the wells. Shorter tubes 98a-98d are positioned at or just above (from about 0 to about 3 mm) top surface, 130, of microchip 18. In use, electrolyte, sample or an internal standard is pumped through tubes 94-97 to near the bottom of wells 47a-47d, while vacuum pump 124 pulls liquid from near the top of the well, thereby both flushing the well and providing a reproducible fill, 132, therefor. Without the use of aspiration to remove liquids, it has been found that a film forms on at least a portion of surface 130, which may disrupt electrical measurements. Fluid manifold 16 is retracted from the surface of the microchip during analysis in order to avoid high-voltage leakage through the pumps during electrophoretic measurements.

Figure 2:
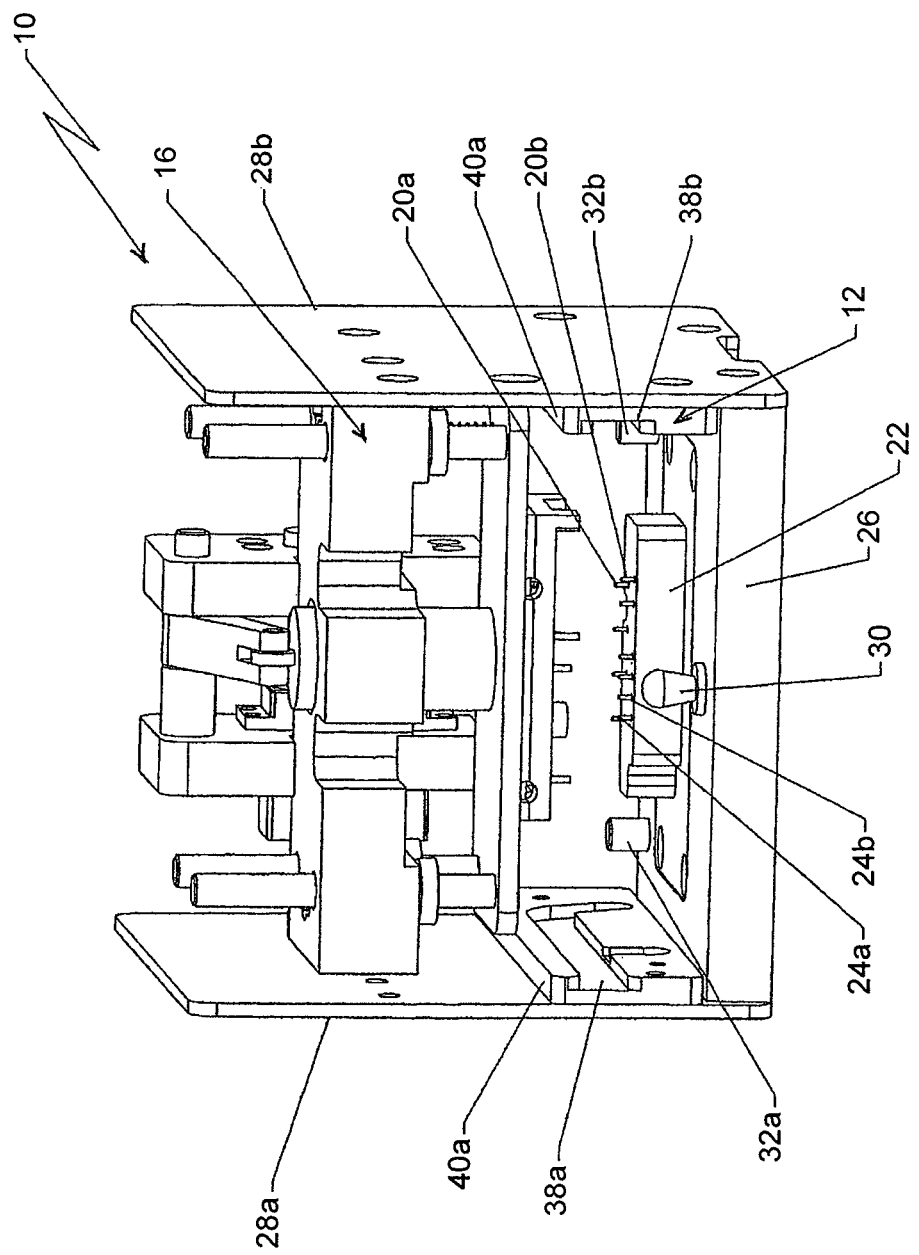
FIG. 2 is a schematic representation of a front perspective view of an embodiment of the microchip interface of the present invention without the microchip and microchip tray in place, showing the microchip tray slide portion, the fluid manifold assembly for providing fluids to the microchip and receiving fluids therefrom disposed in its partially withdrawn position, and the spring-loaded electrical pins adapted for providing voltages to the microchip and for receiving voltages and currents therefrom for measurement.

FIG. 2, is a schematic representation of a front perspective view of an embodiment of microchip interface, 10, of the present invention, showing microchip tray slide portion, 12, for receiving microchip tray, 14, not shown in FIG. 2, and fluid manifold assembly, 16, for providing fluids to microchip, 18, also not shown in FIG. 2, and receiving fluids therefrom disposed in its partially withdrawn position. At least two spring-loaded electrical connections, 20a, and, 20b, mounted in insulating electric bus, 22, provide voltages to microchip 18 from at least one voltage source, not shown in FIG. 2, and/or at least two spring-loaded electrical connections, 24a, and, 24b, also mounted in bus 22 for receiving voltages and currents from microchip 18 for measuring characteristics of the fluids flowing in microchip 18 using measuring apparatus known in the art (not shown in FIG. 2). The locations and functions of pins 20 and 24 depend on the intended application for microchip 18. Insulating block 22, is mounted on base, 26, which supports walls, 28a, and, 28b, to which fluid manifold assembly 16 is mounted.

As will be described in more detail hereinbelow, microchip tray spring stop, 30, stops, 32a, and, 32b, mounted on base 26, rotatable microchip tray wheels, 34a, and, 34b, and, 36a, and, 36b, not shown in FIG. 2, cooperating with channels, 38a, and, 38b, formed in rails, 40a, and, 40b, mounted to walls 28a and 28b, respectively, reversibly hold microchip tray 14 in interface 10. Spring stop 30 may be made from polyurethane, and stops 32a and 32b may be made from a metal, such as steel.

Figure 3:
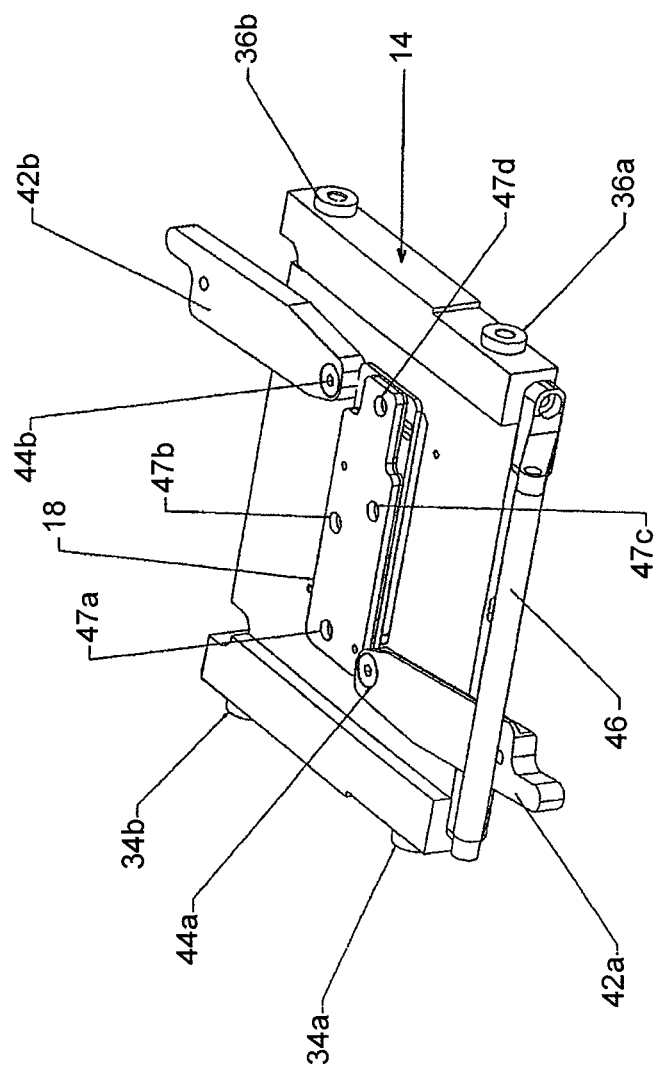
FIG. 3 is a schematic representation of a top perspective view of an embodiment of the microchip tray adapted for insertion into the microchip interface illustrated in FIG. 2, hereof, showing a microchip in place and the microchip clamps in their open position.

FIG. 3 is a schematic representation of a top perspective view of an embodiment of microchip tray 14 adapted for insertion into microchip interface 10 illustrated in FIG. 2 hereof. Microchip clamps, 42a, and, 42b, shown in their open position in FIG. 3, are pivotably connected to tray 14 at locations, 44a, and, 44b. Rotatable wheels, 34a, and, 34b, and 36a, and 36b, are adapted for rolling in channels 38a and 38b, respectively. Handle, 46, is used to direct microchip tray 14 into and out of interface 10. Wells, 47a-47d, in microchip 18 for accessing microfluidic channels therein are also illustrated.

Figure 4:
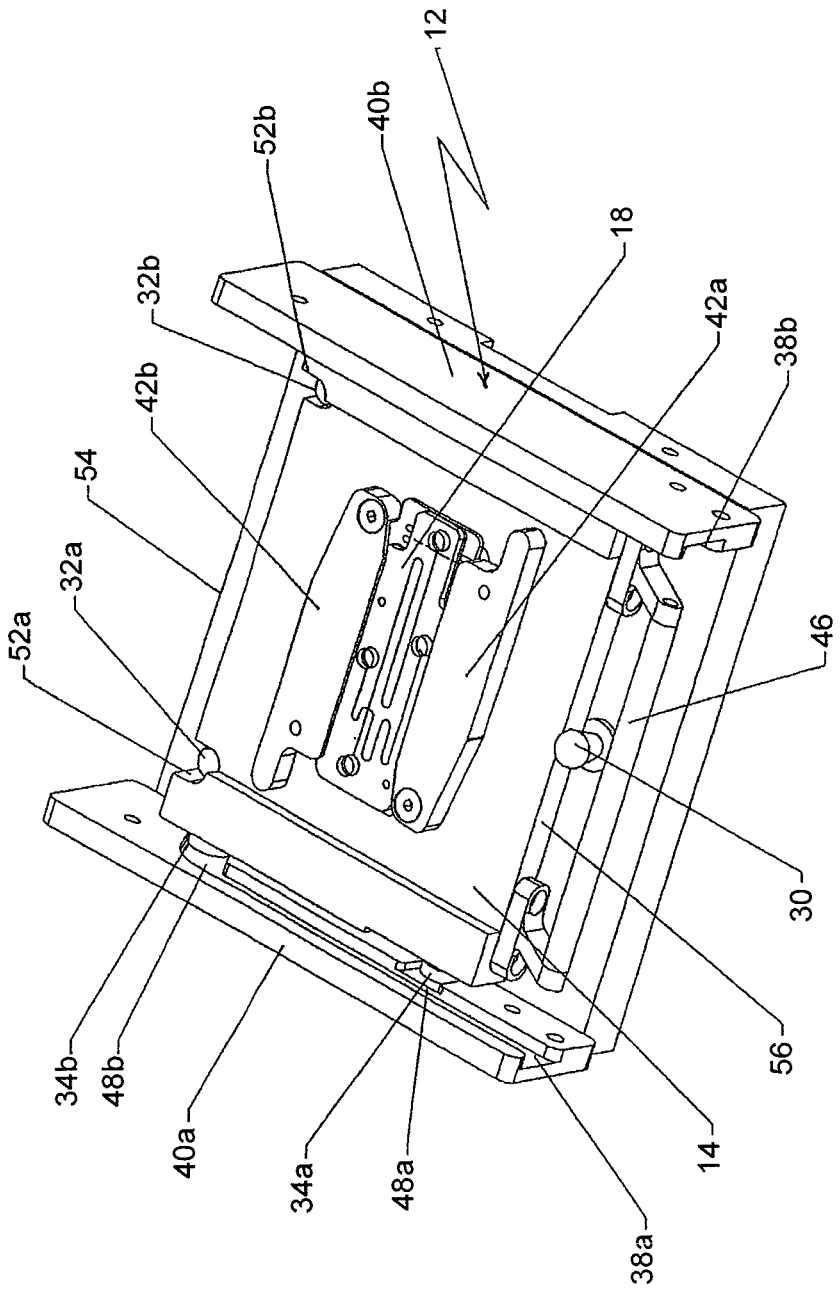
FIG. 4 is a schematic representation of a top perspective view of the microchip tray shown in FIG. 3 hereof, illustrated in its locked-down position in the tray slide portion of the microchip interface shown in FIG. 2 hereof, and with the microchip clamps in their locked position securing a microchip.

FIG. 4 is a schematic representation of a top perspective view of microchip tray 14 shown in FIG. 3 hereof, illustrated in its locked-down position in tray slide portion of microchip interface 10, and with microchip clamps 42a and 42b in their locked position securing microchip 18 onto tray 14. Channel 38a is shown to have two perpendicular sections, 48a, and, 48b, into which wheels 34a and 34b, respectively, may freely move. Similar, opposing perpendicular sections, 50a, and, 50b, not shown in FIG. 3, are formed in channel 38b for receiving wheels 36a and 36b, respectively.

In use, microchip tray 14 bearing locked microchip 18 is slid between rails 40a and 40b in interface 10 such that wheels 34a and 34b and 36a and 36b enter channels 38a and 38b. Tray 14 is pushed forward into interface 10 between rails 40a and 40b until wheels 34a and 34b encounter perpendicular sections 48a and 48b, respectively, and wheels 36a and 36b encounter perpendicular sections 48a and 48b, respectively, at which time tray 14 drops downward such that microchip 18 is in electrical communication with electrical connections 20a and 20b, and/or 24a and 24b on insulated block 22 (FIG. 2, hereof). It should be mentioned that in use, chip 18 is oriented approximately horizontally. Stops 32a and 32b contact slots, 52a, and, 52b, in front wall, 54, of tray 14, and rear wall, 56, of tray 14 contacts spring stop 30, which has sufficient flex to permit tray 14 to reversibly snap into position, such that tray 14 is reversibly secured with electrical contacts in microchip 18, not shown in FIG. 4, in electrical communication with the electrical connections on insulating block 22. Tray 14 may be removed from microchip tray slide portion 12 of interface 10 by grasping handle 46 attached to rear face 56 of microchip tray 14 and pulling microchip tray 14 upward against the spring action of spring stop 30 against wall 56, which permits wheels 34a and 34b, and 36a and 36b to move upwardly in vertical channels 48a and 48b, and 50a and 50b, respectively, and into channels 38a and 38b, respectively, from which tray 14 may be removed from interface 10.

Figure 5:
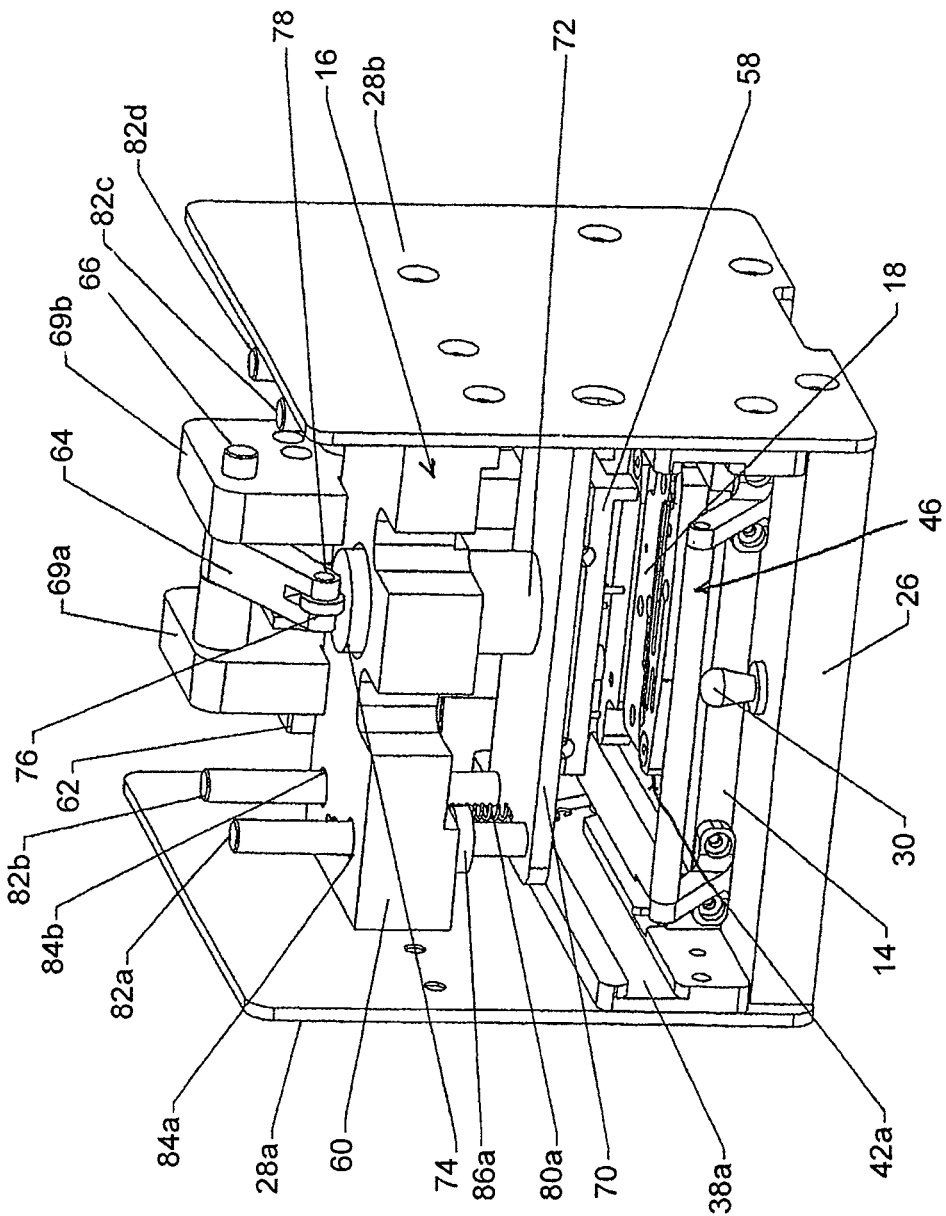
FIG. 5 is a schematic representation of a front perspective view of the embodiment of the microchip interface shown in FIG. 2 hereof, with the microchip and microchip tray shown in FIG. 3 hereof in place, and showing the microchip tray slide portion shown in FIG. 4 hereof, the fluid manifold assembly being disposed in a partially extended position.

FIG. 5 is a schematic representation of a front perspective view of the embodiment of microchip interface 10 shown in FIG. 2 hereof, with the microchip 18 and microchip tray 14 shown in FIG. 3 hereof locked in place in microchip tray slide portion 12 shown in FIG. 4 hereof, and fluid manifold assembly 16 being disposed in a partially extended position. Manifold, 58, is configured to provide fluid transfer to microchip 18 in accordance with the particular application thereof, and pumps and valves as known in the art, but not shown in FIG. 5, suitable for accomplishing this function are provided. Block, 60, attached to walls 28a and 28b, supports motor, 62, which pivots rocker arm, 64, around axle, 66, by rotating cam, 68, not shown in FIG. 4. Axle 66 is supported by mounts, 69a, and, 69b, attached to block 60 and motor 62 is attached to mount 69a. Rocker arm 64 drives spring-loaded manifold mounting plate, 70, to which manifold 58 is attached toward microchip 18, by pushing on pushrod, 72, which travels through hole, 74, in block 60, and is attached to mounting plate 70. Rocker arm bearing, 76, which rotates around axle, 78, in rocker arm 64 facilitates the action of rocker arm 64 on pushrod 72. Springs, 80a, and, 80b, not shown in FIG. 5, attached between block 60 and plate 70, act against the force of pushrod 72 and permit rocker arm 64 to follow cam 68 through the complete rotation thereof. Bearing-mounted guide rods, 82a-82d, attached to mounting plate 70 slide in holes, 84a, and, 84b, and, 84c and, 84d, not shown in FIG. 5, in block 60 through bearings, 86a, and, 86b-86d, not shown in FIG. 5.

Figure 6A:
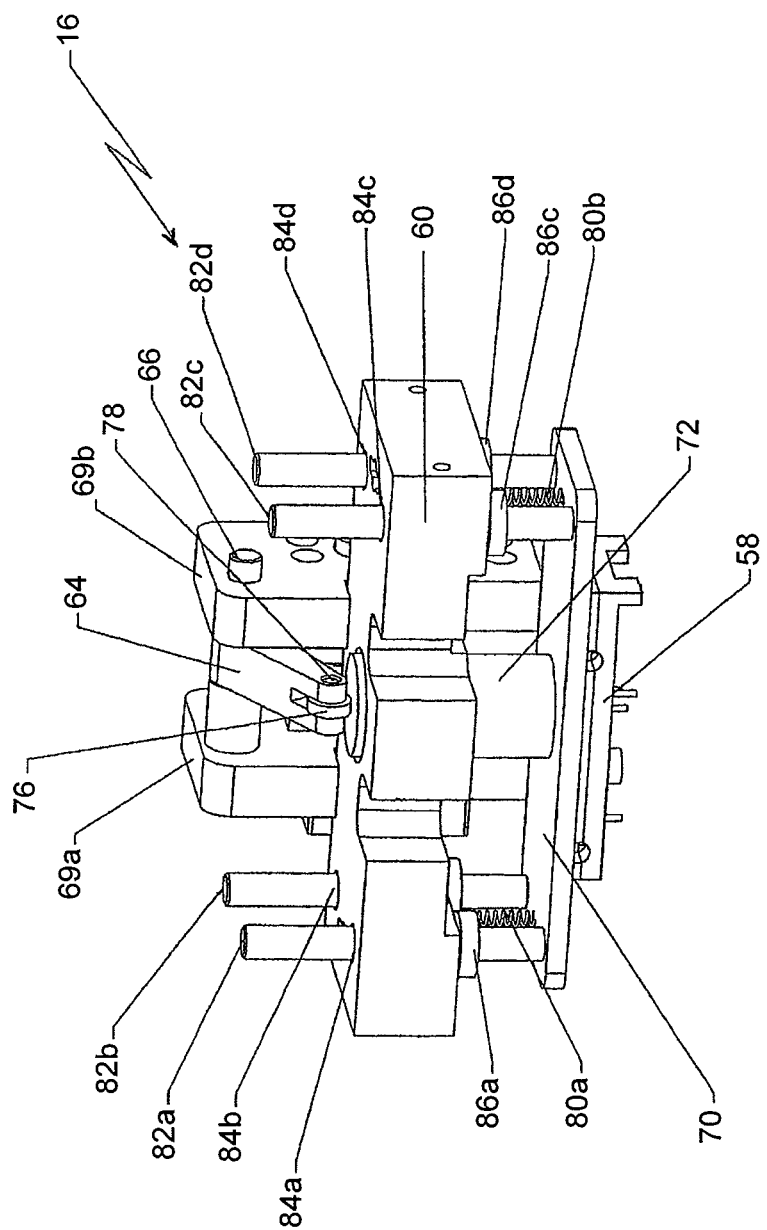
Figure 6B:
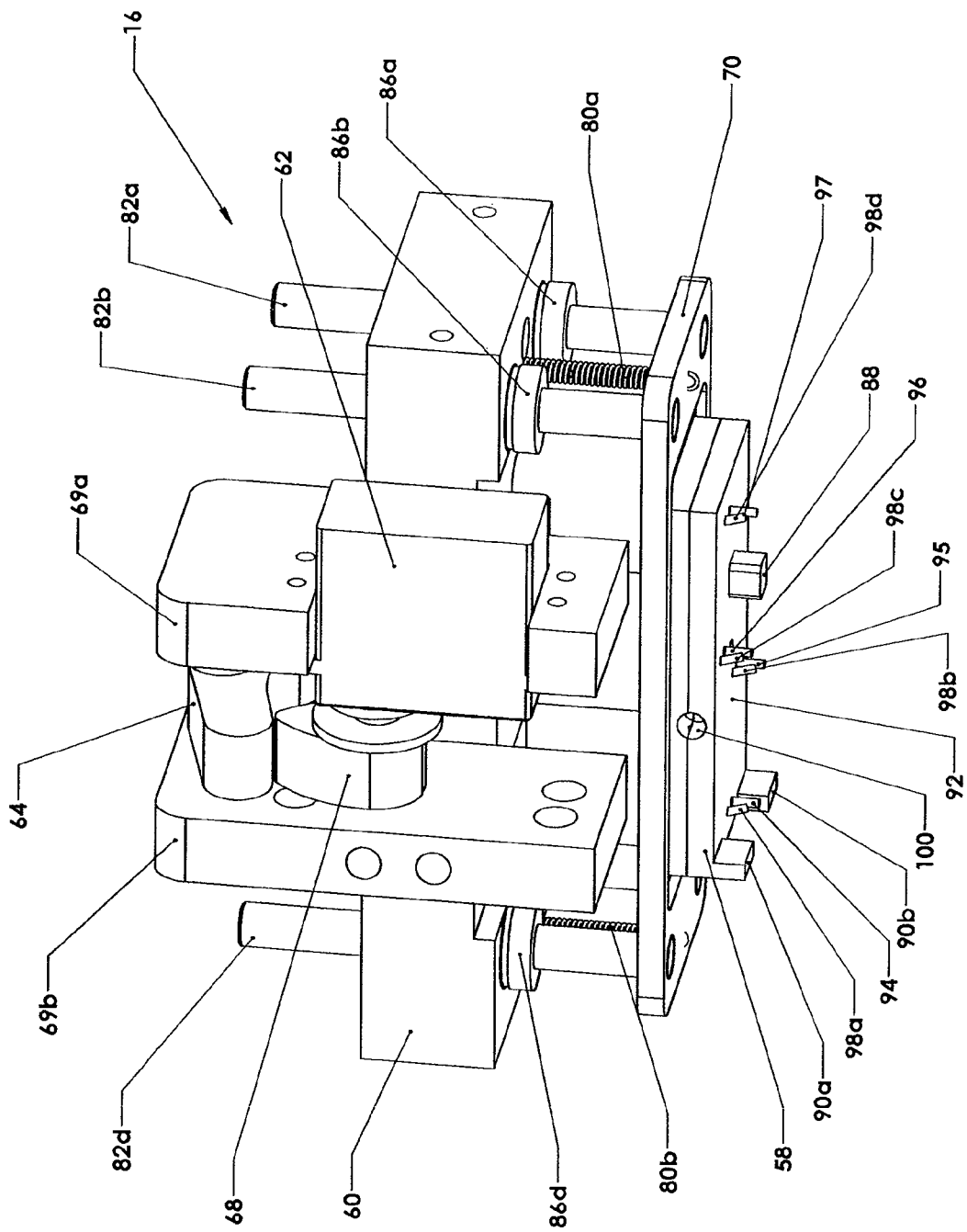
FIG. 6B is a schematic representation of a rear perspective view of the fluid manifold assembly illustrated in FIG. 6A hereof, showing the cam and the motor for rotating the cam which drives the rocker arm and pushrod.

FIG. 6A is a schematic representation of a front perspective view of fluid manifold assembly 16 illustrated in FIG. 2 hereof, showing mounting block 60 for spring-loaded, rocker arm, pushrod-actuated manifold mounting plate 70 and guide rods 82a-82d. FIG. 6B is a schematic representation of a rear perspective view of the fluid manifold assembly 16 illustrated in FIG. 6A hereof, showing motor 62 for rotating cam 68 which pivots rocker arm 64 and pushrod 72. Shown also in FIG. 6B are projections, 88, and, 90a, and, 90b, attached to bottom surface, 92, of manifold 58, for resting on microchip 18 to reproducibly attain the proper spacing between manifold 58 and microchip 18 such that fluid injection tubes, 94, and, 96, and fluid aspiration tubes, 98, are effectively placed in corresponding wells 47a-47d in microchip 18. Port, 100, to which an external source of suction is applied and through which fluids are withdrawn from microchip 18 and directed to suitable waste containers, not shown in FIG. 6B, is connected to aspiration tubes 98 through the body of manifold 58.

In use, fluid manifold assembly, 16, of interface 10 brings fluid manifold 58 into contact with microchip 18. Motor 62 rotates cam 68 such that rocker arm 64 is pivoted and pushes down on pushrod 72 through bearing 76. Pushrod 72 is attached to spring-loaded manifold mounting plate 70 to which manifold 58 is mounted. As stated hereinabove, projections 88, 90a and 90b keep manifold 58 from touching microchip 18 over its entire surface such that injection tubes 94 and 96, and aspiration tubes 98 are properly seated in wells 47a-47d of microchip 18. When measurements are completed, cam 68 is rotated such that the downward pressure on pushrod 72 by rocker arm 64 is reduced. Pushrod 72, rocker arm 64 and cam 68 are all kept in contact in response to the action of springs 80a and 80b which lift manifold mounting plate 70 and manifold 58 away from microchip 18, thereby permitting microchip tray 14 to be removed from interface 10. Motor 62 is chosen such that the force transmitted to manifold 58 cannot break microchip 18.

It should be mentioned that microchip tray 14 bearing microchip 18 is secured in interface 10 before fluid manifold assembly 16 is either lowered to contact microchip 18 or raised away from chip 18.

Figure 7A:
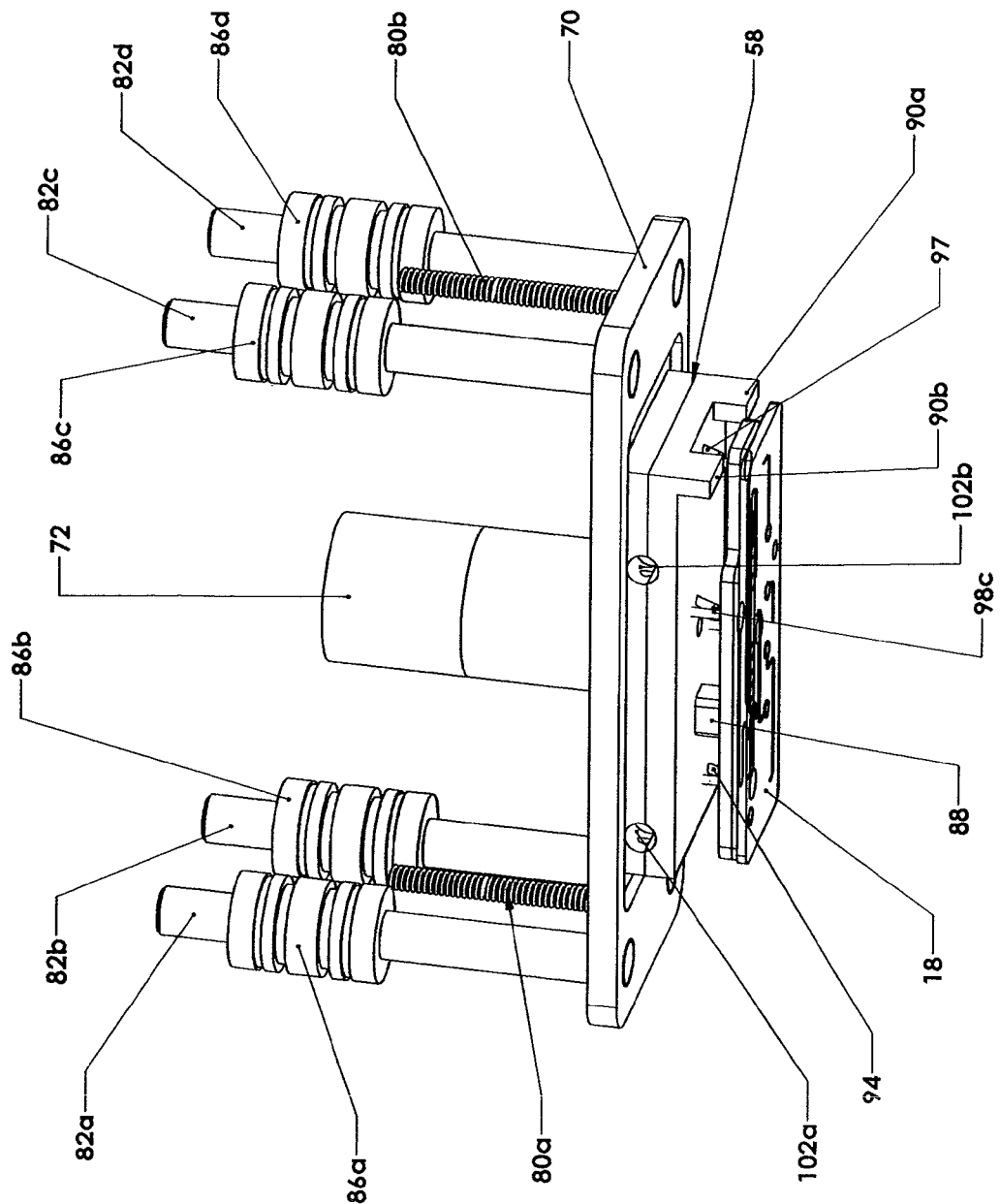
Figure 7B:
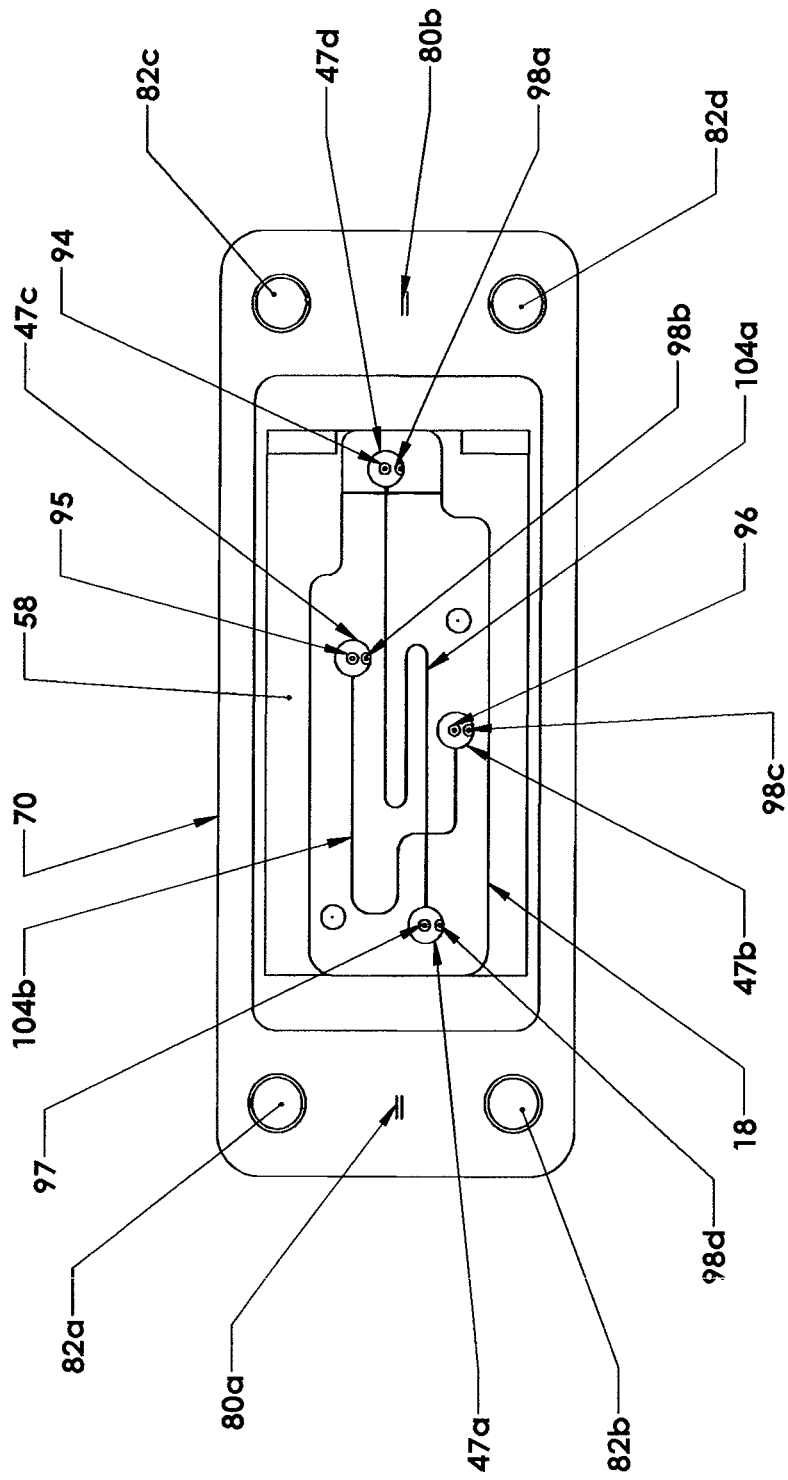
FIG. 7B is a schematic representation of a bottom view of the manifold in proximity to a microchip, and illustrates the injection and aspiration tubes extending into the microchip wells.

FIG. 7A is a schematic representation of a front perspective view of fluid manifold mounting plate 70, with manifold 58 disposed slightly above microchip 18, illustrating the injection tubes 94 and 97 and aspiration tube 98c in proximity to their insertion locations in wells 47a-47d in microchip 18. Shown also are inlet ports 102a and 102b which are connected to injection tubes 94 and 97 through the body of manifold 58, and which are attached to suitable pumps, valves, and fluid sources, not shown in FIG. 7A, depending on the intended application for microchip 18. FIG. 7B is a schematic representation of a bottom view of manifold 58 in proximity to microchip 18, and illustrates injection tubes 94-97 and aspiration tubes 98a-98d extending into microchip wells 47a-47d. Schematic microfluidic channels 104a and 104b are also illustrated in FIG. 7B. As stated hereinabove, manifold 58 contacts microchip 18 through projections 88, and 90a and 90b, and through injection and aspiration tubes 94-97, and 98a-98d, respectively.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for establishing a fluidic and electrical interface to a microfluidic chip having a top surface and at least two wells opening to the top surface, comprising:
    a microchip tray for receiving and holding said microfluidic chip;
    an electrical bus adapted for electrical communication with at least one voltage source and at least one electronic measurement device;
    a microchip tray slide adapted for receiving said microchip tray and placing said microchip into electrical communication with said electrical bus and for reversibly securing said microchip tray and said microchip in electrical communication therewith;
    a fluid manifold assembly for providing chosen fluids to said microchip and for aspirating the chosen fluids from the wells of said microchip, said fluid manifold assembly comprising:
        an electrolyte pump;
        a sample pump;
        a vacuum pump; and
        a fluid manifold comprising:
            at least two liquid dispensing tubes for establishing fluid communication with either said electrolyte pump or said sample pump, and the at least two wells, one of said dispensing tubes in fluid communication with one of the at least two wells; and
            at least two liquid aspiration tubes for establishing fluid communication with said vacuum pump, one of said aspiration tubes in fluid communication with one of the at least two wells;
    a fluid manifold mounting plate for holding said fluid manifold;
    a pushrod having a first end and a second end, the first end of said pushrod affixed to said fluid manifold mounting plate;
    a pivoted rocker arm for driving said pushrod toward or away from said microchip;
    a cam for causing said rocker arm to pivot;
    a motor for rotating said cam; and
    at least one spring for causing said pushrod to follow said rocker arm and said rocker arm to follow said cam;
    whereby said fluid manifold is disposed a chosen distance from said microchip for establishing fluid communication between said at least two liquid dispensing tubes and said at least two liquid aspiration tubes and the at least two wells, and at greater than the chosen distance for electrical measurements.

2. The apparatus of claim 1, wherein said fluid manifold further comprises projections for accurately spacing said manifold at the chosen distance from said microchip.

3. The apparatus of claim 1, wherein said bus further comprises spring-loaded electrical connections adapted for establishing electrical communication between said bus and said microchip.

4. The apparatus of claim 1, wherein each of said at least two liquid dispensing tubes is disposed within one of said at least two wells when said fluid manifold is disposed at the chosen distance from said microchip.

5. The apparatus of claim 4, wherein each of wells has a bottom and each of said at least two fluid dispensing tubes is disposed in the vicinity of the bottom of each of said at least two wells when said fluid manifold is disposed at the chosen distance from said microchip.

6. The apparatus of claim 1, wherein each of said at least two liquid aspiration tubes is disposed near the surface of said microchip in the vicinity of one of the at least two wells when said fluid manifold is disposed at the chosen distance from said microchip.

7. The apparatus of claim 1, further comprising a pump for adding an internal standard to one of said at least one liquid dispensing tubes.

8. Apparatus for establishing a fluidic and electrical interface to a microfluidic chip having a top surface and at least two wells opening to the top surface, comprising:
   a microchip tray for receiving and holding said microfluidic chip;
   an electrical bus adapted for electrical communication with at least one voltage source and at least one electronic measurement device;
   means for placing said microchip into electrical communication with said electrical bus and for reversibly securing said microchip tray and said microchip in electrical communication therewith;
   a fluid manifold assembly for providing chosen fluids to said microchip and for aspirating the chosen fluids from the wells of said microchip, said fluid manifold assembly comprising:
      an electrolyte pump;
      a sample pump;
      a vacuum pump; and
      a fluid manifold comprising:
         at least two liquid dispensing tubes for establishing fluid communication with either said electrolyte pump or said sample pump, and the at least two wells, one of said dispensing tubes in fluid communication with one of the at least two wells; and
         at least two liquid aspiration tubes for establishing fluid communication with said vacuum pump, one of said aspiration tubes in fluid communication with one of the at least two wells;
   means for moving said fluid manifold to a chosen distance from said microchip for establishing fluid communication between said at least two liquid dispensing tubes and said at least two liquid aspiration tubes and the at least two wells, and to a greater than the chosen distance for electrical measurements.

9. The apparatus of claim 8, wherein said fluid manifold further comprises projections for accurately spacing said manifold at the chosen distance from said microchip.

10. The apparatus of claim 8, wherein said bus further comprises spring-loaded electrical connections adapted for establishing electrical communication between said bus and said microchip.

11. The apparatus of claim 8, wherein each of said at least two liquid dispensing tubes is disposed within one of said at least two wells when said fluid manifold is disposed at the chosen distance from said microchip.

12. The apparatus of claim 11, wherein each of the at least two wells has a bottom and each of said at least two fluid dispensing tubes is disposed in the vicinity of the bottom of each of said at least two wells when said fluid manifold is disposed at the chosen distance from said microchip.

13. The apparatus of claim 8, wherein each of said at least two liquid aspiration tubes is disposed near the surface of said microchip in the vicinity of one of the at least two wells when said fluid manifold is disposed at the chosen distance from said microchip.

14. The apparatus of claim 8, further comprising a pump for adding an internal standard to one of said at least one liquid dispensing tubes.

15. The apparatus of claim 8, where said means for means for moving said fluid manifold to a chosen distance from said microchip comprises: a fluid manifold mounting plate for holding said fluid manifold; a pushrod having a first end and a second end, the first end of said pushrod affixed to said fluid manifold mounting plate; a pivoted rocker arm for driving said pushrod toward or away from said microchip; a cam for causing said rocker arm to pivot; a motor for rotating said cam; and at least one spring for causing said pushrod to follow said rocker arm and said rocker arm to follow said cam.

16. A method for providing a fluidic and an electrical interface for a microfluidic chip having a top surface at least two wells opening to the top surface, comprising:
   placing the microchip into electrical communication with an electrical bus capable of electrical communication with at least one voltage source and at least one electronic measurement device;
   reversibly securing the microchip in electrical contact with the bus;
   providing chosen fluids to the wells of the microchip using a fluid manifold having one injection tube and one aspiration tube for each well;
   moving the fluid manifold to a chosen distance from the secured microchip, whereby each injection tube is disposed in its corresponding well, and each aspiration tube is disposed near the surface of the microchip in the vicinity of a well, such that fluid does not spill onto the top surface of the microchip during said step of providing chosen fluids to the wells, and to a greater than the chosen distance for electrical measurements.

17. The method of claim 16, wherein the fluid manifold further comprises projections for accurately spacing said manifold at the chosen distance from the microchip.

18. The method of claim 16, wherein the electrical bus further comprises spring-loaded electrical connections adapted for establishing electrical communication between the bus and the microchip.

19. The method of claim 16, wherein each of the liquid dispensing tubes is disposed within one of the at least two wells when the fluid manifold is disposed at the chosen distance from the microchip.

20. The method of claim 19, wherein each of the at least two wells has a bottom and each of the liquid dispensing tubes is disposed in the vicinity of the bottom of each of the wells when the fluid manifold is disposed at the chosen distance from the microchip.

21. The method of claim 16, wherein each of the liquid aspiration tubes is disposed near the surface of the microchip in the vicinity of a well when the fluid manifold is disposed at the chosen distance from the microchip.

* * * * *